United States Patent
Fialkoff

(10) Patent No.: US 7,094,217 B2
(45) Date of Patent: Aug. 22, 2006

(54) BRASSIERE FOR EXPRESSING BREAST MILK

(75) Inventor: Steven Fialkoff, New York, NY (US)

(73) Assignee: Medela Holding AG, Baar (CH)

( * ) Notice: Subject to any disclaimer, the term of this patent is extended or adjusted under 35 U.S.C. 154(b) by 0 days.

(21) Appl. No.: 08/629,381

(22) Filed: Apr. 8, 1996

(65) Prior Publication Data

US 2003/0167037 A1 Sep. 4, 2003

(51) Int. Cl.
*A61M 1/06* (2006.01)
*A41C 3/04* (2006.01)

(52) U.S. Cl. .......................................... 604/74; 450/36
(58) Field of Classification Search .................. 450/36, 450/58, 37; 604/73–76
See application file for complete search history.

(56) References Cited

U.S. PATENT DOCUMENTS

| | | | |
|---|---|---|---|
| 949,414 A * | 2/1910 | Cunningham | |
| 2,440,466 A | 4/1948 | Freedman | 2/42 |
| 2,501,860 A | 3/1950 | Becker | 2/42 |
| 2,679,048 A * | 5/1954 | Alberts | |
| 2,715,225 A * | 8/1955 | Gould | 450/58 |
| 2,890,702 A * | 6/1959 | Farino | |
| 2,925,816 A | 2/1960 | Rosenthal | 128/461 |
| 4,004,294 A * | 1/1977 | Pinch | 450/36 X |
| 4,270,538 A | 6/1981 | Murphy | 128/282 |
| 4,355,641 A | 10/1982 | Dastoli et al. | 128/460 |
| 4,390,024 A | 6/1983 | Williams | 128/460 |
| 4,411,269 A | 10/1983 | Weintraub | 128/482 |
| 4,550,734 A * | 11/1985 | Porco | 450/36 |
| 4,633,876 A * | 1/1987 | Scullin | 450/36 |
| 4,640,287 A * | 2/1987 | Anderson et al. | 450/36 |
| 4,713,842 A | 12/1987 | Patterson | 2/104 |
| 4,878,879 A * | 11/1989 | Kunstadter | |
| 4,911,677 A | 3/1990 | White | 450/36 |
| 5,024,628 A | 6/1991 | Sanchez | 450/36 |
| 5,038,411 A | 8/1991 | St. Armand | 2/104 |
| 5,090,059 A | 2/1992 | Kahl | 2/104 |
| 5,094,647 A | 3/1992 | Courtney | 450/36 |
| 5,278,998 A | 1/1994 | Book | 2/102 |
| 5,309,572 A | 5/1994 | Seamans | 2/112 |
| 5,380,238 A * | 1/1995 | Crew-Gee | 450/36 |
| 5,514,166 A * | 5/1996 | Silver et al. | 450/36 X |
| 5,575,768 A * | 11/1996 | Lockridge et al. | |
| 6,379,327 B1 * | 4/2002 | Lundy | |

FOREIGN PATENT DOCUMENTS

DE 584 456 9/1933

* cited by examiner

*Primary Examiner*—Mark Bockelman
(74) *Attorney, Agent, or Firm*—Baniak Pine & Gannon

(57) ABSTRACT

A brassiere for supporting the breasts of a wearer and for receiving and supporting a funnel for expressing breast milk, comprising a pair of cups, at least one of which includes a first portion and a second portion having at least one elastic band. The first and second portion, and of the cup are expandable to allow a funnel to be selectively inserted between said first portion and said second portion, and under said first portion, and under said second portion, so as to contact said breast for expressing milk.

14 Claims, 4 Drawing Sheets

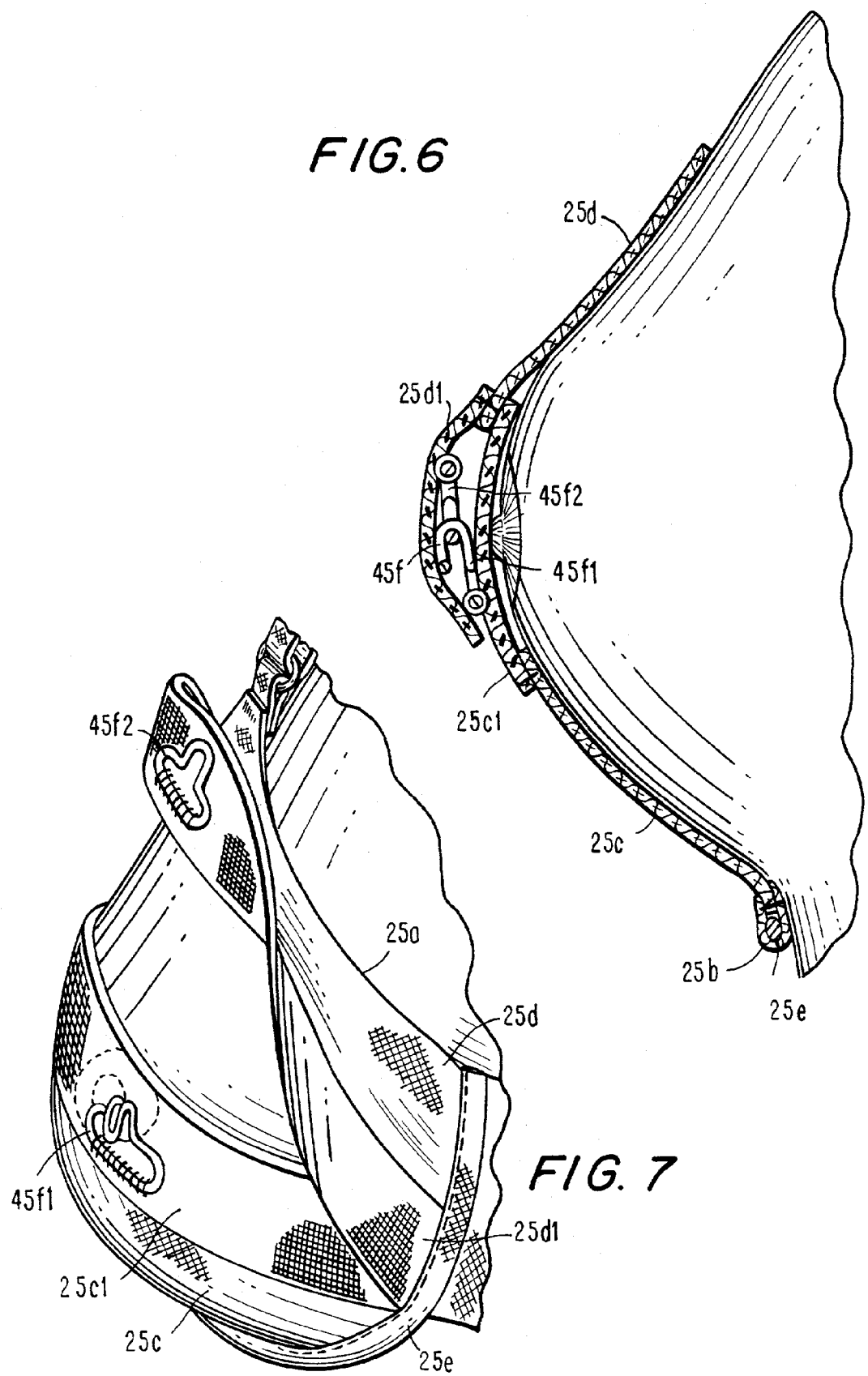

BRASSIERE FOR EXPRESSING BREAST MILK

BACKGROUND OF THE INVENTION

The present invention relates to an improved brassiere for supporting the breasts of the wearer and for receiving and supporting a funnel for expressing breast milk that may be stored for later consumption by an infant.

At one time, the majority of mothers nourished their new-born infants by breast-feeding, but over the years, the trend changed to feeding infants with formula. Today, medical doctors recognize that infant formula is not sophisticated enough to supplant the benefits of breast milk, in part because the content of breast milk changes based on the infant's nutritional needs. For this reason, increasing numbers of women are once again breast feeding their children.

A woman who is nursing an infant typically will express breast milk to store for times when she is unable or unavailable to breast feed her infants. A woman expresses her milk by using an electric or manual pumping device in conjunction with a funnel, which the woman holds tightly against her nipple to create suction and to direct the flow of milk into a storage container. Often because of the length of time required to express milk, when using a pump, a woman will express both breasts simultaneously. To express both breasts, the woman must hold a funnel with each hand against her breasts, leaving her sitting in an awkward position, unable to enjoy other activities. The prior art does not solve this problem.

In the past, brassieres for breast feeding typically were made so as to allow a nursing infant access to the woman's breast. A typical example of this type of brassiere is disclosed in U.S. Pat. No. 2,501,860, which shows a brassiere with cups that allow an infant access to the woman's breasts by means of a flap that may be folded back. The infant gains access when the wearer folds back the cup flap thereby revealing an orifice formed by multiple pieces of material and reinforced by stitching.

A similar construction is disclosed in U.S. Pat. No. 2,925,816, which reveals a brassiere constructed with a flap that may be folded down from its normal position to give an infant access to the wearer's breast. The brassiere supports the breast when the flap is folded down by three portions of connected material. Once again, the material of the cup, which remains when the flap is folded down, is reinforced by stitching. This prior-art brassiere also allows a woman to insert a pad into the inside of the cup to absorb bodily excretions.

U.S. Pat. No. 2,440,466 discloses a similar brassiere with the ability to receive an absorbing pad that may also be used to enhance a woman's appearance. The cup is formed of three panels, a top and bottom panel and a reinforcing panel. The pad is attached to the reinforcing panel, which holds the pad in its proper position.

While prior-art brassieres allow an infant access to a woman's breast, they are not constructed to receive and support a funnel that can be attached to a breast pump to allow a woman to express breast milk. For the foregoing reasons, there is a need for a brassiere designed to allow fast, easy, and secure attachment of a funnel attached to a pump for expressing milk.

SUMMARY OF THE INVENTION

Generally speaking, the present invention is a brassiere for supporting the breasts of a wearer and for receiving and supporting a funnel for expressing breast milk. The brassiere is provided with at least one cup with an expandable opening in the center that easily stretches to allow a funnel to be inserted and at the same time supports the funnel, thereby freeing the woman's hands for doing other things. The brassiere is comprised of a pair of cups dimensioned to substantially cover a woman's breasts. The cups have an upper edge and an arcuate or curved edge. A connecting portion joins the cups at the inside of the curved edges of the cups. A back support is connected to the outer edge of the curved edges of the cups. At least one of the cups includes at least two portions that are each attached to the cup along the curved edge. These portions are positioned such that they are not attached at their common border. Elastic bands are attached to each of the two portions along their common border. A funnel may be selectively inserted between and under the first and second portions of the cups and positioned so as to contact a woman's breast for creating suction by means of a pump to express milk. With the funnel inserted, the elastic bands close back over the funnel mouth of the funnel to provide a snug and secure fit and support the funnel in its breast-contacting position. With the funnel or funnels firmly in place, the wearer may now express milk without holding the storage containers.

Accordingly, it is an object of the present invention to provide an improved brassiere for use in expressing breast milk.

It is another object of the invention to provide a brassiere, constructed to free a woman's hands to do other activities while she expresses breast milk, by supporting a funnel that creates suction and directs the flow of milk into a storage container.

It is a further object of the present invention to provide a brassiere with expandable openings that both allows a funnel to be positioned to express breast milk and supports the funnel when it is in the expressing position.

It is still a further object of the present invention to provide a brassiere for expressing milk that may be used as any other brassiere when not being used to express milk.

Still other objects and advantages of the invention will in part be obvious and will in part be apparent from the specification.

The invention accordingly comprises an article of manufacture possessing the features, properties, and the relation of elements which will be exemplified in the article hereinafter described, and the scope of the invention will be indicated in the claims.

BRIEF DESCRIPTION OF THE DRAWINGS

For a fuller understanding of the invention, reference is had to the following description taken in connection with the accompanying drawings, in which:

FIG. 6 is an enlarged sectional view taken along line 6—6 of FIG. 5; and

FIG. 7 is a perspective view of an embodiment of the brassiere in an unlatched position constructed in accordance with the second embodiment of the present invention.

DETAILED DESCRIPTION OF THE PREFERRED EMBODIMENTS

Figure 1:
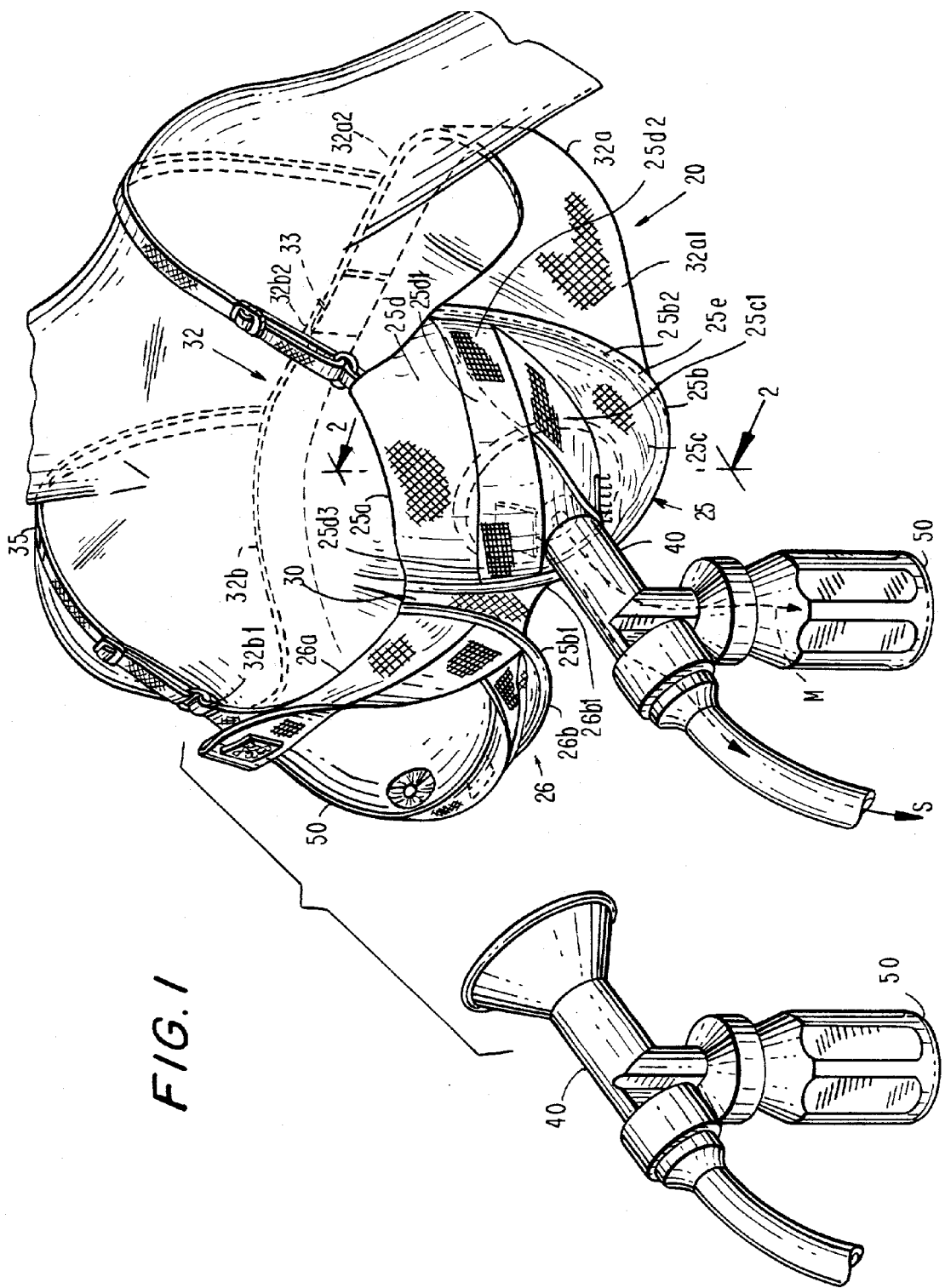
FIG. 1 is a perspective view of the brassiere with funnel and storage container constructed in accordance with a first embodiment of the present invention.
Figure 2:
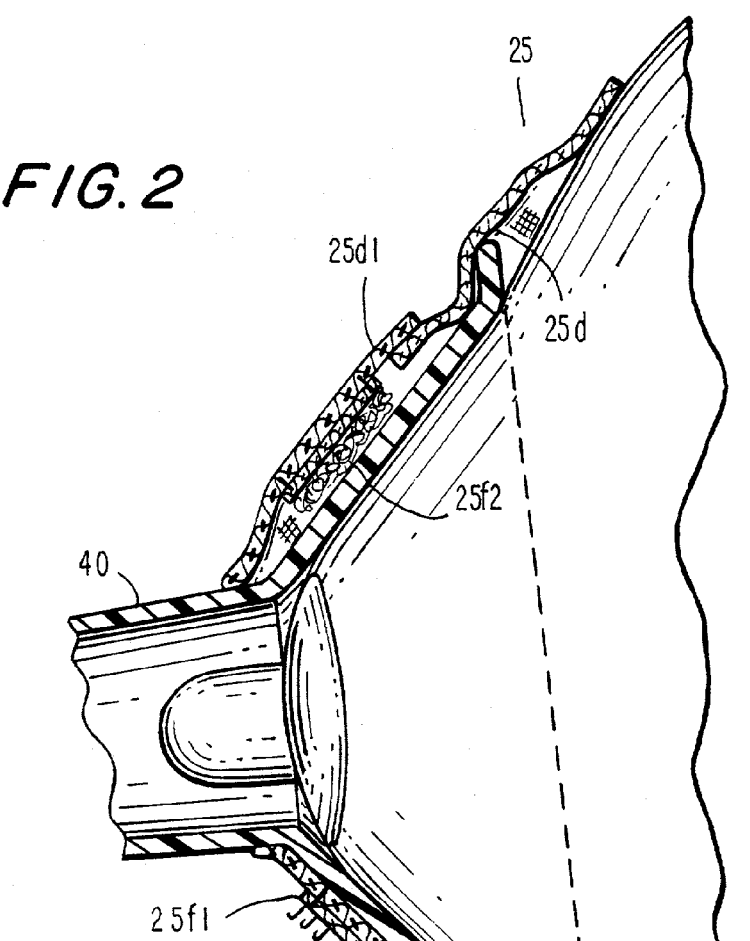
FIG. 2 is an enlarged sectional view taken along line 2—2 of FIG. 1.
Figure 3:
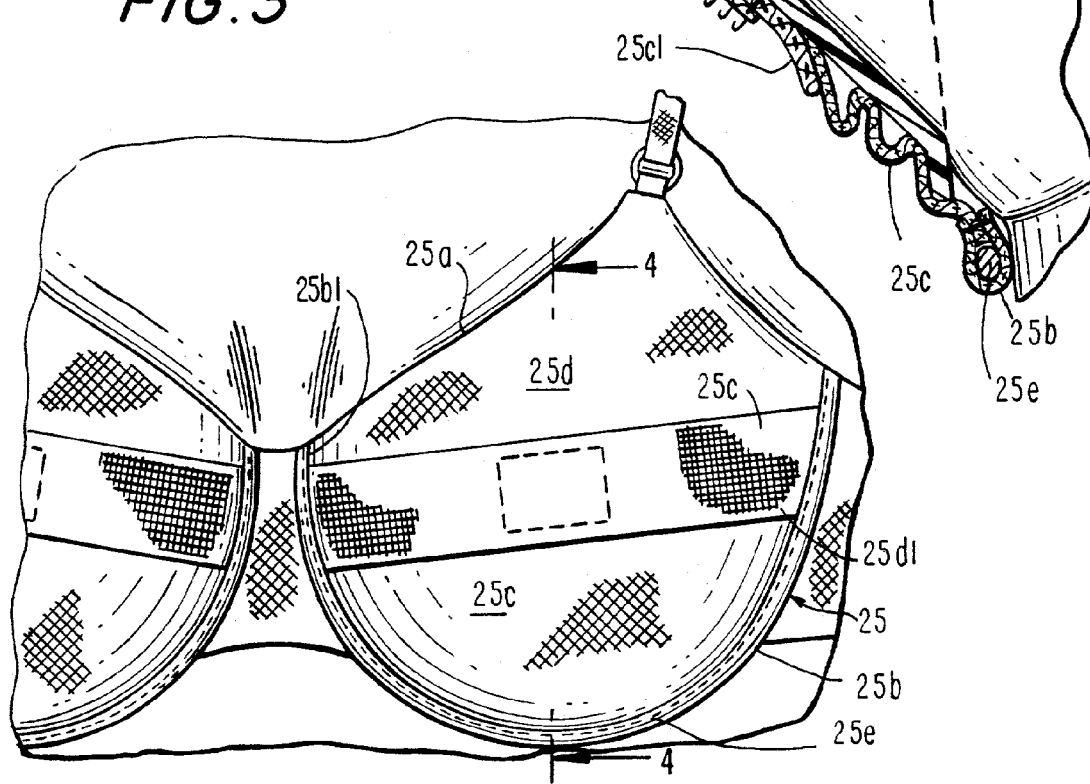
FIG. 3 is an enlarged partial front elevational view of the brassiere in the non-expressing position constructed in accordance with a first embodiment of the present invention.

Referring now to FIG. 1, a brassiere, generally indicated at 20, and constructed in accordance with a first preferred embodiment, is disclosed. Brassiere 20 includes a first cup 25 and a second cup 26, a connector portion 30, and a back support 32. Connector portion 30 is sewn to an inner side 25$b$1 of arcuate edge 25$b$ of first cup 25 and an inner side 26$b$1 of arcuate 26$b$ of second cup 26, thereby connecting first cup 25 and second cup 26. Connector portion 30 may be made of a flexible material, such as Spandex, lace, or loosely knit cotton.

Back support 32 includes a first wing 32$a$ and a second wing 32$b$. First wing 32$a$ is formed with a first end 32$a$1, which is sewn to an outer side 25$b$2 of an arcuate edge 25$b$ of first cup 25, and a second end 32$a$2. Similarly, second wing 32$b$ is made up of a first end 32$b$1, which is sewn to an outer side 26$b$ of an arcuate edge 26$b$1 of second cup 26, and a second end 32$b$2. A releasable clasp 33 joins second end 32$a$2 of first wing 32$a$ to second end 32$b$2 of second wing 32$b$. Thus, when the wearer joins together clasp 33, brassiere 20 becomes one contiguous piece consisting of first wing 32$a$, second wing 32$b$, second cup 26, first cup 25, and connecting portion 30.

Shoulder straps 35 are used to further hold the brassiere on the wearer. Straps 35 are adjustably attached to cups 25 and 26 and first and second wings 32$a$ and 32$b$. As an alternative to clasp 33, wings 32$a$ and 32$b$ may be a single piece of material. In this arrangement, connector portion 30 includes a clasp for releasably connecting cup 25 to cup 26, so that, when the clasp is joined together, the brassiere becomes one contiguous piece consisting of back portion 32, first cup 25, connector 30 and second cup 26.

Referring now to FIGS. 1–4, first cup 25 is formed with an upper edge 25$a$, arcuate edge 25$b$, a first portion 25$c$, which functions as a lower flap, a second portion 25$d$, which functions as a upper flap, a first elastic band 25$c$1 and second elastic band 25$d$1. Upper edge 25$a$ is connected to arcuate edge 25$b$. Arcuate edge 25$b$ may be reinforced along its entire length or for part of its length by, for example, an underwire 25$e$. The arcuate edge of first portion 25$c$ is sewn to arcuate edge 25$b$. The curved outer edges of second portion 25$d$ are sewn to inner side 25$b$1 of arcuate edge 25$b$. First elastic band 25$c$1 is sewn to an upper edge of first portion 25$c$. A first band end (not shown) of first elastic band 25$c$1 is sewn to outer side 25$b$2 of arcuate edge 25$b$ and a second band end (not shown) of first elastic band 25$c$1 is sewn to inner side 25$b$1 of arcuate edge 25$b$. Similarly, second elastic band 25$d$1 is sewn to the lower edge of second portion 25$d$. A first band end 25$d$2 of second elastic band 25$d$1 is sewn to outer side 25$b$2 of arcuate edge 25$b$ and a second band end 25$d$3 of second elastic band 25$d$1 is sewn to inner side 25$b$1 of arcuate edge 25$b$. In this manner, when brassiere 20 is in an unflexed condition, elastic bands 25$c$1 and 25$d$1 overlap each other along their entire length.

Alternatively, first band 25$c$1 and second band 25$d$1 may be positioned essentially anywhere about cup 25 so long as they substantially overlap their midpoint is over the nipple of the breast. For example, first band end (not shown) of first elastic band 25$c$1 and first band end 25$d$2 of second elastic band 25$d$1 may be sewn to upper edge 25$a$ at a point located between the outer side 25$b$2 of arcuate edge 25$b$ and the location where shoulder strap 35 connects to upper edge 25$a$.

Figure 4:
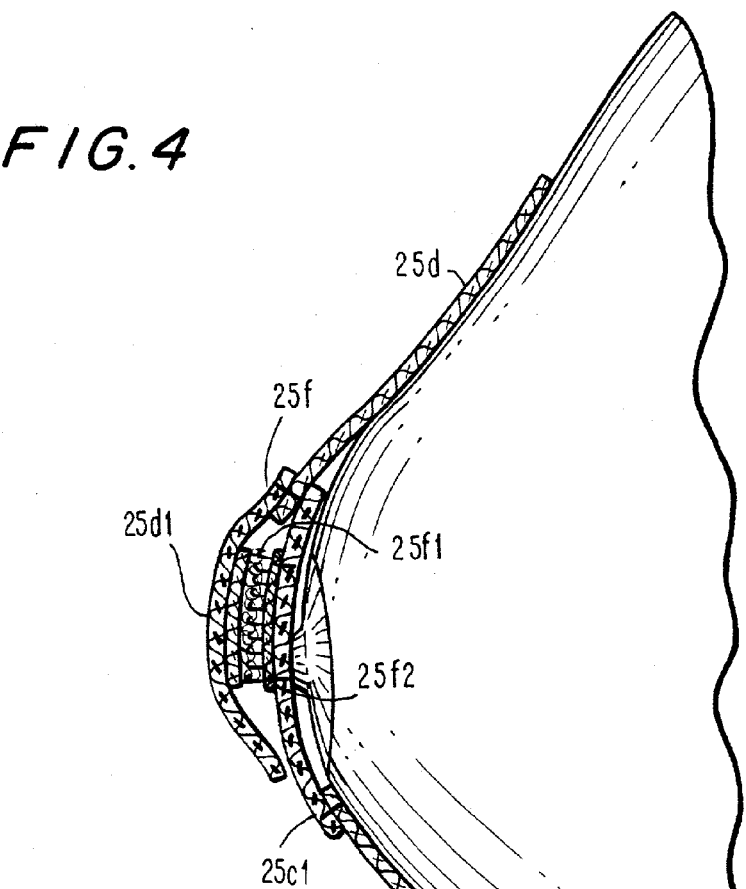
FIG. 4 is an enlarged sectional view taken along line 4—4 of FIG. 3.

A latch 25$f$ best shown in FIG. 4 is further provided to secure first portion 25$c$ and second portion 25$d$ to one another when the wearer is not expressing breast milk. More specifically, latch 25$f$ consists of a first latch element 25$f$1 and a second latch element 25$f$2. First latch element 25$f$1 is affixed to a lower surface of elastic band 25$d$1 of first portion 25$d$. Second latch element 25$f$2 is affixed to the upper surface of elastic band 25$c$1 of second portion 25$c$. Latch 25$f$ may consist of hook and loop elements, commonly known as VELCRO® fastener (FIGS. 2–4), or any other means of securing elastic bands 25$c$1 and 25$d$1 when the wearer wears the brassiere in its non-expressing position.

Second cup 26 is constructed in a manner similar to first cup 25. Second cup 26 is made up of an upper edge 26$a$, an arcuate edge 26$b$, a first portion 26$c$, which functions as a lower flap, a second portion 26$d$, which functions as an upper flap, a first elastic band 26$c$1 and a second elastic band 26$d$1. Upper edge 26$a$ is connected to arcuate edge 26$b$. Arcuate edge 26$b$ may be reinforced along its entire length or for part of its length by, for example, an underwire 26$e$. The arcuate edge of first portion 26$c$ is sewn to arcuate edge 26$b$. The curved outer edges of second portion 26$d$ are sewn to inner side 26$b$1 of arcuate edge 26$b$. First elastic band 26$c$1 is sewn to an upper edge 26$c$4 of first portion 26$c$. A first band end (not shown) of second elastic band 26$c$1 is sewn to outer side 26$b$2 of arcuate edge 26$b$ and a second band end (not shown) of second elastic band 26$c$1 is sewn to inner side 26$b$1 of arcuate edge 26$b$.

Similarly, a second elastic band of second cup 26 is sewn to the lower edge of the second portion of second cup 26. A first band end of the second elastic band of cup 26 is sewn to the outer side of arcuate edge 26$b$ and a second band end of the second elastic band of second cup 26 is sewn to inner side 26$b$1 of arcuate edge 26$b$. In this manner, when brassiere 20 is in an unflexed condition, the first and second elastic bands of second cup 26 overlap each other along their entire length.

Figure 5:
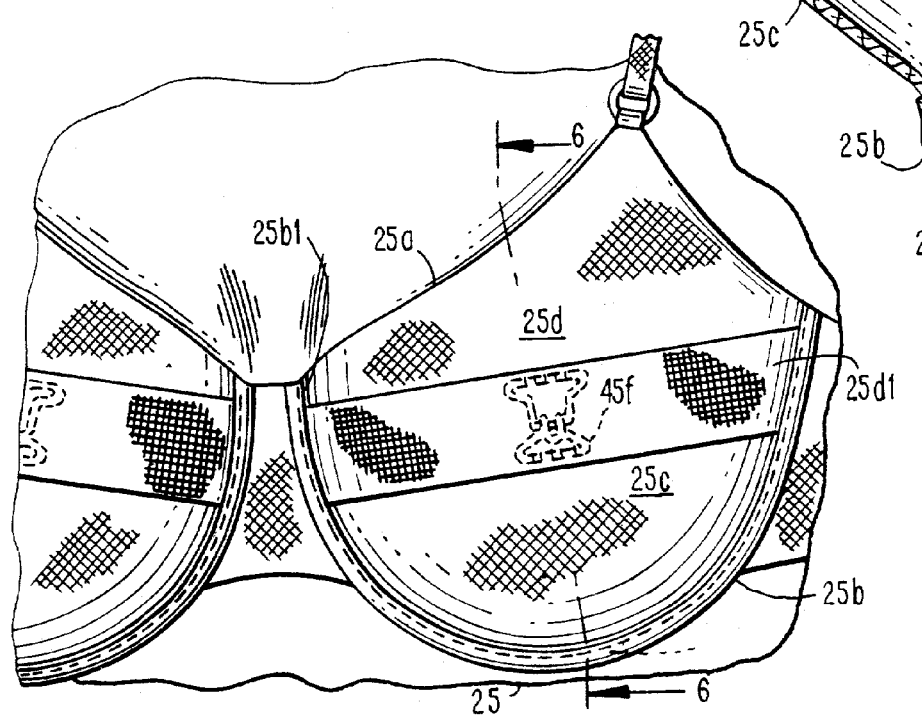
FIG. 5 is an enlarged front elevational view of the brassiere in the non-expressing position constructed in accordance with a second embodiment of the present invention.

FIGS. 5–7 disclose another embodiment of the invention, like numbers being used to denote like parts. In place of latch 25$f$, a latch 45$f$ is used to secure first portion 25$c$ and second portion 25$d$ one to the other when the wearer is not expressing breast milk. In this embodiment, latch 45$f$ consists of a clasp. More specifically, clasp 45$f$ consists of a first clasp element 45$f$1 and a second clasp element 45$f$2. First latch element 45$f$1 is affixed to a lower surface of elastic band 25$c$1 of first portion 25$c$. Second latch element 45$f$2 is affixed to the upper surface of elastic band 25$d$1 of second portion 25$d$. As with the hook and loop fastener of latch 25$f$ described above, when the wearer desires to express breast milk, funnel 40 (FIG. 2) is inserted between and under first portion 25$c$ and second portion 25$d$, and elastic bands 25$c$1 and 25$d$1 are positioned such that funnel 40 forms a seal about the breast so that breast milk may be expressed. When finished, funnel 40 is removed and latch 45$f$ is hooked together in a conventional fashion so that first portion 25$c$ and second portion 25$d$ are held together to support properly the wearer's breast.

When the wearer wishes to use brassiere 20 for expressing breast milk from one breast (cup 25 will be used in this example but the operation for cup 26 is identical), latch 25$f$ (FIG. 4) or 45$f$ (FIG. 6) is separated and a funnel 40 is inserted between and under first portion 25$c$ and second portion 25$d$. In this position, elastic bands 25$c$1 and 25$d$1 solely support the funnel in its expressing position. The elastic force of bands 25c1 and 25d1 maintain the seal created between funnel 40 and the wearer's breast. When the wearer activates the pump (not shown), suction is created in the direction of arrow S (FIG. 1) that draws breast milk from the wearer's nipple into funnel 40 (direction of arrow M) and deposits the expressed breast milk in container 50. Thus, rather than holding the funnel to her breast, the wearer is free to do other activities.

When the express process is completed, funnel 40 is simply removed from under first portion 25c and second portion 25d, and elastic bands 25c1 and 25d1 are positioned such that first latch element 25f1 becomes secured to second latch element 25f2. In this manner, first portion 25c and second portion 25d are held together to properly support the wearer's breast. First portion 25c and second portion 25d may be formed of a suitably flexible, relatively thin material, such as Spandex, lace, or loosely knit cotton.

Similarly, the wearer may express her breast milk from both breasts simultaneously. In this configuration, the wearer positions funnel 40 within cup 25 and another funnel within cup 26. This method allows the woman to express breast milk more efficiently. That is, the wearer can express twice the milk in the same amount of time, while still having her hands free to do other things.

Of course, brassieres may be constructed such that only one cup is constructed to accept a funnel. Therefore, a brassiere may have one cup that is constructed in a manner known in the art and one (either cup 25 or cup 26) constructed as described above.

It will thus be seen that the objects set forth above, among those made apparent from the preceding description, are efficiently attained and, since certain changes may be made in the above constructions without departing from the spirit and scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. A method for supporting a breast shield on a breast, comprising the following steps:
   providing a garment member;
   providing an opening defined by a reinforced area of material carried on the garment member and which overlies the breast shield for mounting the breast shield to the garment member; and
   mounting the breast shield to the garment member using the material such that a portion of the breast shield passes through the opening and is supported on the breast without need of manually supporting the breast shield in use, wherein the breast shield is separate from the garment member and otherwise usable without employment of the garment member, wherein said garment member comprises a brassiere-type garment having a bra cup with a detachable flap for exposing the breast.

2. The method of claim 1, wherein the step of mounting comprises sliding the breast shield through said flap with said material being carried on a part of said flap.

3. A brassiere for supporting the breasts of a wearer and for receiving and supporting a funnel for expressing breast milk, comprising a pair of cups, said pair of cups dimensioned to substantially cover said breasts, each of said pair of cups having an upper edge and a lower edge;
a connecting portion for joining said pair of cups;
a back support affixed to said pair of cups;
at least one of said pair of cups including a first portion and a second portion, said first portion having one end attached to the lower edge of one of said pair of cups and a free end, said second portion having an end attached to the upper edge of one of said pair of cups and a free end;
a first elastic band being affixed to said free end of said first portion;
whereby said funnel may be selectively inserted between said first portion and said second portion and under said first portion and said second portion, so as to contact said breast for expressing milk.

4. The brassiere of claim 3, further including a second elastic band affixed to said free end of said second portion.

5. The brassiere of claim 4, further comprising a pair of shoulder straps, said pair of shoulder straps each having a first end and a second end, said first end of one of said pair of shoulder straps being affixed to said upper edge of one of said pair of cups, said first end of one of the other of said pair of shoulder straps being affixed to said upper edge of the other of said pair of cups, said second end of each of said pair of shoulder straps being affixed to said back support.

6. The brassiere of claim 4, wherein said back portion is comprised of a first wing part and a second wing part, said first wing part and said second wing part each having a first end and a second end, said first end of said first wing part being attached to said lower edge of one of said pair of cups, said first end of said second wing part being attached to said lower edge of the other of said pair of cups, said first wing part second end and said second wing part second end being releasably attached to one another by means of a latch.

7. The brassiere of claim 6, further comprising a pair of shoulder straps, said pair of shoulder straps each having a first end and a second end, said first end of one of said pair of shoulder straps being affixed to said upper edge of one of said pair of cups, said first end of one of the other of said pair of shoulder straps being affixed to said upper edge of the other of said pair of cups, said second end of one of said pair of shoulder straps being affixed to said first wing part, said second end of the other of said pair of shoulder straps being affixed to said second wing part.

8. The brassiere of claim 3, wherein said first portion and said second portion of at least one of said pair of cups may be selectively affixed one to the other by means of a connector.

9. The brassiere of claim 8 further comprising a second elastic band affixed to said free end of said second portion, and said connector further comprising a latch having a first latch element and a second latch element, said first latch element being affixed to said first elastic band, said second latch element being affixed to said second elastic band, said first latch element and said second latch element being selectively attached one to the other to affix said first portion and said second portion of said at least one of said pair of cups one to the other.

10. A method of using a brassiere for supporting the breasts of a wearer and for receiving and supporting a funnel for expressing breast milk, said brassiere having a pair of cups, at least one cup of said pair of cups including a first portion and a second portion, said first portion and said second portion each having a free end, at least one of said free ends having an elastic band, comprising the steps of:

separating at least a part of said free end of said first portion from at least a part of said free end of said second portion to form an opening;

inserting said funnel into said opening, under said first portion, and under said second portion of said cup of said brassiere so as to contact said breast;

holding said funnel against said breast by means of said elastic band to substantially form a seal between said funnel and said breast;

activating a pump to create suction at the breast nipple to cause breast milk to be expressed; and directing said breast milk into a storage container.

11. A method of using a brassiere for supporting the breasts of a wearer and for receiving and supporting a funnel for expressing breast milk, the brassiere having a pair of cups, at least one cup of the pair of cups including a first portion and a second portion, the first portion and the second portion each having a free end, each of the free ends having an elastic band, comprising the steps of:

separating at least a part of the free end of the first portion from at least a part of the free end of the portion to form an opening;

inserting the funnel into the opening, under the first portion, and under the second portion of the cup of the brassiere so as to contact the breast;

holding the funnel against the breast by means of both elastic bands to substantially form a seal between the funnel and the breast;

activating a pump to create suction at the breast nipple to cause breast milk to be expressed; and directing the breast milk into a storage container.

12. A method of using a brassiere for supporting the breasts of a wearer and for receiving and supporting a funnel for expressing breast milk, said brassiere having a pair of cups, at least one cup of said pair of cups including a first portion and a second portion, said first portion and said second portion each having a free end, each of said free ends at least partially overlapping one another and at least one of said free ends having an elastic band, comprising the steps of:

releasing a latch attaching said first portion and said second portion of said cup;

separating at least a part of said free end of said first portion from at least a part of said free end of said second portion to form an opening;

inserting said funnel into said opening, under said first portion, and under said second portion of said cup of said brassiere so as to contact said breast;

holding said funnel against said breast by means of said elastic band to substantially form a seal between said funnel and said breast;

activating a pump to create suction at the breast nipple to cause breast milk to be expressed; and directing said breast milk into a storage container.

13. A method of using a brassiere for supporting the breasts of a wearer and for receiving and supporting a funnel for expressing breast milk, the brassiere having a pair of cups, at least one cup of the pair of cups including a first portion and a second portion, the first portion and the second portion each having a free end, each of the free ends having an elastic band, comprising the steps of:

releasing a latch attaching the first portion and the second portion of the cup;

separating at least a part of the free end of the first portion from at least a part of the free end of the second portion to form an opening;

inserting the funnel into the opening, under the first portion, and under the second portion of the cup of the brassiere so as to contact the breast;

holding the funnel against the breast by means of both elastic bands to substantially form a seal between the funnel and the breast;

activating a pump to create suction at the breast nipple to cause breast milk to be expressed; and directing the breast milk into a storage container.

14. A method for supporting a breast shield on a breast, comprising the following steps:

providing a garment member;

providing an opening defined by a reinforced area of material carried on the garment member and which overlies the breast shield for mounting the breast shield to the garment member; and mounting the breast shield to the garment member using the material such that a portion of the breast shield passes through the opening and is supported on the breast without need of manually supporting the breast shield in use, wherein the breast shield is separate from the garment member and otherwise usable without employment of the garment member, wherein said opening is expandable and is defined by stretchable material.

* * * * *